United States Patent [19]

Faggian et al.

[11] 4,278,602
[45] Jul. 14, 1981

[54] PROCESS FOR SYNTHESIZING PYRAN NITRILES

[75] Inventors: Lucio Faggian; Edoardo Platone, both of San Donato Milanese, Italy

[73] Assignee: Anic S.p.A., Palermo, Italy

[21] Appl. No.: 94,599

[22] Filed: Nov. 15, 1979

[30] Foreign Application Priority Data

Dec. 19, 1978 [IT] Italy ............................. 30986 A/78

[51] Int. Cl.³ .......................................... C07D 309/08
[52] U.S. Cl. ................................................. 260/345,1
[58] Field of Search ..................................... 260/345.1

[56] References Cited

U.S. PATENT DOCUMENTS 4,150,037  4/1979  Prevedello et al. ............... 260/345.1

OTHER PUBLICATIONS

Meinwald, JACS, 77, 1617 (1955).

Primary Examiner—Nicky Chan
Attorney, Agent, or Firm—Morgan, Finnegan, Pine, Foley & Lee

[57] ABSTRACT

The present invention relates to a process for synthesizing pyran nitriles of the general formula

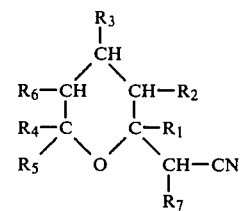

consisting of reacting aliphatic 1,5 hydroxyketones with aliphatic nitriles in the presence of basic substances such as oxides, hydroxides, and carbonates of alkali metal and alkaline earth metals, and in particular of alkali metal hydroxides or alcoholates, as the catalyst.

5 Claims, No Drawings

PROCESS FOR SYNTHESIZING PYRAN NITRILES

The present invention relates to a process for synthesizing pyran nitriles of general formula

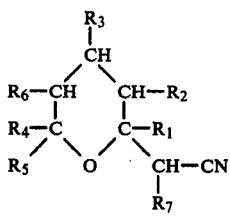

consisting of reacting aliphatic 1,5 hydroxyketones with aliphatic nitriles in the presence of basic substances such as oxides, hydroxides, and carbonates of alkali metals and alkaline earth metals, and in particular of alkali metal hydroxides or alcoholates, as catalysts.

The reaction scheme is as follows

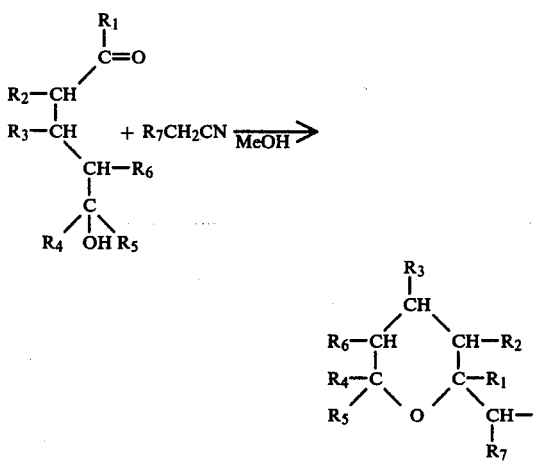

In the above formulas, $R_2$, $R_3$, $R_4$, $R_5$, $R_6$ and $R_7$ are H, —$CH_3$, alkyl, alkylaryl, arylalkyl, aryl or cycloalkyl, and can be the same or different from each other, $R_1$ can be defined as the preceding radicals but can never be hydrogen.

It is known to use pyran nitriles as components of perfumes (U.S. Pat. No. 4,150,037 of Apr. 17, 1979 of Snamprogetti S.p.A.; Chem. Abstr. 85 (1976) 192564 m).

The syntheses described previously for these products required several steps, some of which are carried out under exacting conditions (e.g. low temperature, use of valuable bases in stoichiometric quantity, alternate steps with basic and acid catalysts, and the consequent need of adequate separation and purification of reaction intermediates).

On the other hand, the general methods described in the literature (see Houben-Weyl, Methoden der Organischen Chemie, vol. VI-4, page 12 onwards) for the synthesis of tetrahydropyrans (without the substituent

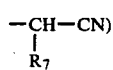

cannot be used for synthesising the products described by us, unless the synthesis is carried out in a number of steps as stated heretofore.

The synthesis of products which are homologues of those described by us only in the formal sense (see Berichte 38, 1502 (1905); J.Am.chem.Soc. 77, 1617 (1955)) cannot be applied in our case, in that it uses catalysis and reactivity which are limited to the case described by the said authors, and which are completely inoperative with our substrates, as proved by comparative tests carried out by us and given among the examples in the present text.

In contrast, with the process according to the present invention, it is possible to obtain cyclic nitriles in a single step, under reaction conditions which can be easily set up and using limited quantities of non-valuable catalysts. The starting substances are easily available aliphatic hydroxyketones, which can be prepared for example by the processes described in the pending U.S. Patent Application Ser. No. 829,878 filed on Sept. 1, 1977, now abandoned, and the U.S. Patent Application Ser. No. 937,869 filed on Aug. 29, 1978 which was abandoned in favor of continuation application Ser. No. 139,765, filed Apr. 14, 1980 of the present applicant.

As stated, the reaction which enables pyran nitriles to be obtained according to our invention is carried out in a single step.

It is conducted in the presence of an alkali metal hydroxide, preferably KOH, which although it can be used in stoichiometric quantity with respect to the hydroxyketone, is advantageously used (with the benefit both of improved yield and process economy) in a molar ratio of 1/5 to 1/1000 to the hydroxyketone, the molar base/hydroxyketone ratio preferably being between 1/100 and 15/100.

As an alternative to the alkaline hydroxide, an alkaline alcoholate can be used as catalyst.

It has been found experimentally that the molar aliphatic nitrile/hydroxyketone ratio can lie in the range of 2 to 100, preferably 5 to 30.

The reaction is advantageously carried out in a temperature range of 30° to 150° C., preferably 50° to 120° C., either at atmospheric pressure or under pressure, according to the requirements determined by the reagents and the prechosen temperature.

A further characteristic of the process according to the present invention is that on separating the unreacted hydroxyketone and the produced pyran nitrile in the final reaction mixture by distillation, the residue from this distillation contains products which if introduced into a second reaction with fresh hydroxyketone, are in their turn converted into pyran nitrile, so improving the reaction yield.

The pyran nitrile can be used either as such or as an intermediate for the preparation of valuable products such as geranonitrile, hydroxygeranonitrile, furan nitriles etc. The following examples illustrate the field of application of our invention, but without limiting it.

EXAMPLE 1

41 g (1 mole) of freshly distilled acetonitrile and 0.65 g of 86% potassium hydroxide (0.01 moles) are placed in a 250 ml flask fitted with a mechanical glass bladed stirrer, thermometer, dry nitrogen inlet and a 50 ml filling funnel, and also provided with a Vigreux distillation column with a top thermometer, condenser, calibrated test tube for collecting the distillate, and a silica gel guard tube.

After careful inerting with dry nitrogen, the stirrer is switched on and heating is begun with an electric heating jacket until boiling.

14.85 g of 97% 2-methyl-heptan-2-ol-6-one (MEPTA) (0.1 moles) are fed from the filler funnel over 30 minutes.

Heating is adjusted so that the head of the distillation column is always lapped by vapour.

During the test, which lasts 3 hours, 2.5 ml of liquid are distilled over.

The boiler temperature rises during the test from 82° to 86° C. Afterwards, the reaction mixture is cooled rapidly while maintaining it under a light flow of nitrogen, and is then poured into a beaker containing 100 ml of stirred water and ice.

The reaction mixture is then neutralised with a 1 N aqueous solution of HCl, checking the final point with a glass/calomel electrode connected to a Metrohm potentiograph.

The reaction mixture is transferred into a separating funnel, the organic phase is separated and the aqueous phase is extracted with six 50 cc portions of ethyl ether.

The ether extracts are added to the organic phase, and then dried by contact with anhydrous $Na_2SO_4$.

After 16 hours, the $Na_2SO_4$ is filtered through Gooch, and the sodium sulphate is washed with two 50 cc portions of anhydrous ethyl ether.

The wash ether is added to the organic phase. The ether is distilled under vacuum (500 Torr) with a Vigreux column of $\phi$ 1", h=30 cm until a temperature of 50° C. is reached in the boiler.

The distillation residue is weighed, and analysed by gas chromatograph (Hewlett & Packard 5836 A; columns 3.5 m SE30 4% through GASCHROM P SIL., temperature programmed from 80° to 160° C.; and 2.5 m LAC 728 15% through CHROM.W washed with acids, temperature programmed from 80° to 160° C.) using the internal standard method and correcting the chromatographic areas by the respective corrective factors obtained with synthetic mixtures.

The gas chromatography analysis has to be carried out through two columns, so that by combining the results obtained, any interference is eliminated.

3.587 g (0.0215 moles) of 2,6,6-trimethyl-2-cyanomethyltetrahydropyran and 4.132 g of unreacted MEPTA are obtained.

The hydroxyketone conversion is 71.3%, and the pyran nitrile yield (with respect to the hydroxyketone introduced into the reaction) is 21.5 mol %.

EXAMPLE 2

53.3 g of freshly distilled acetonitrile (1.3 moles) and 0.17 g of 86% potassium hydroxide (0.0026 moles) are placed in the apparatus described in example 1.

The apparatus is inerted with dry nitrogen, and is then heated to boiling with the stirrer running.

A solution of 3.86 g of 97% purity 2-methyl-heptan-2-ol-6-one (0.026 moles) in 11.5 g of acetonitrile are fed into the reactor over 30 minutes.

5.5 ml of product are distilled over during the course of the reaction.

The boiler temperature is maintained at 82°–83° C.

After 3 hours of reaction, heating is suspended, and a light flow of carbon dioxide is fed in while at the same time cooling the reactor by immersing it in a water and ice bath.

The mixture is then filtered through Gooch, and the apparatus and residue on the filter are washed with a little anhydrous methanol.

The mixture is then concentrated by distillation under vacuum in a Vigreux column (100 Torr, boiler temperature=35° C.). The residue in the boiler is washed with two 10 ml portions of water.

The wash water is extracted with ten 10 ml portions of ethyl ether.

The ether extracts are added to the organic phase, dried by contact with $Na_2SO_4$, and then concentrated by distillation in a Vigreux column at 450 Torr until a temperature of 42° C. is attained in the boiler.

A residue is obtained which, when analysed as in example 1, is found to contain 0.953 g of unreacted hydroxyketone and 1.414 g of 2,6,6-trimethyl-2-cyanomethyltetrahydropyran. The hydroxyketone conversion is 74.5%, and the pyran nitrile yield (with respect to the hydroxyketone introduced into the reaction) is 32.6 mol %.

EXAMPLE 3

Comparative example: reaction carried out in the absence of the basic catalyst.

41 g of acetonitrile (1 mole) are placed in the apparatus described in the preceding examples. It is brought to boiling under stirring, and 14.8 g of 97.3% purity 2-methyl-heptan-2-ol-6-one (0.1 moles) are added over 30 minutes.

The temperature in the reactor is maintained at 85° C. so as not to distil the product.

After 27 hours the reaction is suspended, the reaction mixture is discharged, the reactor is washed with anhydrous ethyl ether, the ethyl ether is added to the reaction mixture, and this is concentrated by distillation under vacuum (500–400 Torr) until a temperature of 50° C. is reached in the boiler.

The distillation residue is weighed, and analysed by the method already described. 86.2% of the hydroxyketone is found to have undergone no change.

No pyran nitrile is detected by gas chromatography analysis under the conditions used, nor by mass spectrometry of the reaction products.

EXAMPLE 4

Comparative example: reaction carried out using a weak acid instead of the basic catalyst.

41 g of acetonitrile (1.0 moles) and 0.6183 of orthoboric acid (0.01 moles) are placed in the described apparatus. After inerting with nitrogen, stirring is begun and heating is then carried out until boiling.

14.8 g of 97.3% 2-methyl-heptan-2-ol-6-one (0.1 moles) are then fed over 30 minutes.

The reaction temperature is maintained at 85° C. so as not to distil the product.

After 24 hours, the reaction is stopped.

The reaction mixture is cooled rapidly under a light flow of nitrogen, and is then poured into a beaker containing 100 ml of stirred water and ice.

The reaction flask is washed several times with a little water, which is then added to the reaction mixture. It is then neutralised with an aqueous sodium bicarbonate solution.

The mixture is then extracted with ethyl ether in a separating funnel.

The ether extracts are added together and are dried over anhydrous sodium sulphate. Most of the ether is distilled off under vacuum, and the residue is weighed and analysed by gas chromatography in the usual manner.

88.4% of the initial hydroxyketone is found to be unchanged. No pyran nitrile is detectable by gas chromatograph analysis under the conditions used, nor by mass spectrometry examination of the mixture on termination of the reaction.

EXAMPLE 5

2.6 g of 86% potassium hydroxide (0.04011 moles), 164 g of acetonitrile (4.0 moles) and 59.4 g of 97% 2-methyl-heptan-2-ol-6-one (0.400 moles) are placed in a 1 liter stainless steel autoclave fitted with an oil circulation jacket, pressure gauge and thermometer well, and also provided with a distillation column complete with a thermometer well at its top, condenser and distillate collection vessel.

After closing the autoclave, a tightness test is carried out by pressuring with dry nitrogen. Nitrogen inerting is then carried out, and the pressure is reduced to atmospheric pressure. The stirrer system, consisting of a soft iron bar coated with teflon and driven magnetically, is set into motion, and silicone oil at a temperature of 105° C. is fed into the autoclave jacket from a temperature controlled bath by the bath pump.

After 10 minutes, the temperature in the autoclave reaches 100° C., and from this moment the reaction proceeds for 1 hour. Every 15 minutes, a small amount of the inerts is bled from the distillate collection vessel.

During the tests, the pressure is kept between 1.1 and 1.5 kg/cm$^2$ gauge, and the temperature at 100° C.

On termination of the test, cooling is effected by passing cold water through the reactor jacket, the reactor is then discharged and the product is treated in the manner described in example 1.

On gas chromatography analysis, the final sample is found to contain 12.7 g of hydroxyketone and 19.775 g of 2,6,6-trimethyl-2-cyanomethyltetrahydropyran (0.1184 moles).

The hydroxyketone conversion is 78.0%, and the pyran nitrile yield (with respect to the hydroxyketone introduced into the reaction) is 29.6 mol %.

EXAMPLES 6 to 10

The results shown in the table given hereinafter were obtained using the apparatus and method of example 1.

| EXAMPLE NO. | MOL RATIO CH$_3$CN/ MEPTA/ KOH | TEMP °C. | TEST DURATION HOURS | MEPTA CONV. % | PYRAN NITRILE YIELD MOL % |
| --- | --- | --- | --- | --- | --- |
| 6 | 10/1/0.287 | 82–85 | 3 | 91.4 | 27.0 |
| 7 | 10/1/0.945 | 83–87 | 3 | 97.5 | 20.8 |
| 8 | 20.5/1/0.125 | 82–84 | 3 | 74.0 | 27.0 |
| 9 | 20.5/1/0.194 | 82–85 | 3 | 83.8 | 28.8 |
| 10 | 20.5/1/0.517 | 82–85 | 3 | 94.1 | 27.7 |

EXAMPLE 11

41 g of freshly distilled acetonitrile (1.0 moles) and 4.0 g of sodium hydroxide (0.1 moles) are placed in the apparatus described in example 1.

After inerting with dry nitrogen, it is brought to boiling under stirring, and 14.95 g of 2-methyl-heptan-2-ol-6-one (0.104 moles) are fed over 1 hour.

15 cc of product distilled off in 6 hours of reaction. The reaction mixture is then subjected to the various treatments described in example 1.

From gas chromatography analysis it is found that the hydroxyketone conversion is 80.1%.

The yield of 2,6,6-trimethyl-2-cyanomethyltetrahydropyran is 13.8 mol % with respect to the hydroxyketone introduced into the reaction.

EXAMPLE 12

The process is carried out exactly as described in example 1. The KOH is replaced by 1.182 g (0.01 moles) of potassium ter-butylate.

On termination of the reaction, and after carrying out the described treatments, 5.87 g of unreacted hydroxyketone and 3.51 g of 2,6,6-trimethyl-2-cyanomethyltetahydropyran are present.

The hydroxyketone conversion is 59.3%, and the pyran nitrile yield is 21 mol % with respect to the hydroxyketone introduced into the reaction.

EXAMPLE 13

Example of a process in which the reaction by-products are recycled.

5.2380 g of 86% potassium hydroxide (0.08081 moles), 330 g of recently distilled acetonitrile (8.0488 moles) and 118.8 g of 97.59% 2-methyl-heptan-2-ol-6-one (0.80512 moles), all carefully dried, are placed in a Brignole stainless steel 1 liter autoclave fitted with a magnetically driven stirrer, thermometer well, dip tube and pressure gauge and heated by means of electrical heater elements embedded in a block of high-conductivity light alloy, and further fitted with a coil for circulating cooling water.

After closing, carrying out a tightness test and inerting with dry nitrogen, the stirrer is started and the temperature is raised to 100° C.

The time for reaching this temperature is 30 minutes, and the reaction temperature is maintained at 100° C. for 1 hour after which cooling is carried out rapidly with water down to ambient temperature.

The reaction mixture is transferred into the boiler of a Vigreux and Claisen distillation apparatus fitted with a collector for collecting the fractions.

The reaction mixture is distilled under vacuum, heating it by means of an oil bath.

A first fraction is collected at 56° C./300 Torr consisting of acetonitrile, then a further fraction is collected at about 1 Torr/75°–85° C. consisting almost essentially of 2,6,6-trimethyl-2-cyanomethyltetrahydropyran together with the unconverted hydroxyketone.

The distillation residue, still containing a little pyran nitrile and other reaction products which can be further converted, is dissolved in 57.6 g of acetonitrile, the insoluble part is separated by filtration and the solution is recycled into the autoclave for a new reaction after adding 122.7 g of 94.5 weight % 2-methyl-heptan-2-ol-6-one (0.80525 moles), 5.2737 g of 86% KOH (0.08137 moles) and 272.4 g of acetonitrile. After the reaction, and after distilling exactly in the manner already described, 62.22 g of 2,6,6-trimethyl-2-cyanomethyltetrahydropyran (0.41451 moles) together with the unconverted hydroxyketone are recovered in the distillate.

The distillation residue of the second reaction is again recycled for a third synthesis after adding a further 122.7 g of 94.5% 2-methyl-heptan-2-ol-6-one (0.80525 moles), 5.2853 g of 86% KOH and acetonitrile in the usual ratio. After the reaction, distillation gives 82.0 g of 2,6,6-trimethyl-2-cyanomethyltetrahydropyran (0.49099 moles) in the distillate, together with the unconverted hydroxyketone.

Taking an overall evaluation of the second and third reaction (which simulate a plant operating with recycle but without recycling the hydroxyketone), a 2,6,6-trimethyl-2-cyanomethyltetrahydropyran yield of 52.9 mol % is obtained with respect to the 2-methyl-heptan-2-ol-6-one introduced into the reaction. As the hydroxyketone conversion during each test is about 80%, it is foreseeable that the overall pyran nitrile yield would rise to around 66 mol % if the unconverted hydroxyketone was also recycled.

We claim:

1. A process for synthesizing pyran nitriles of the formula (I):

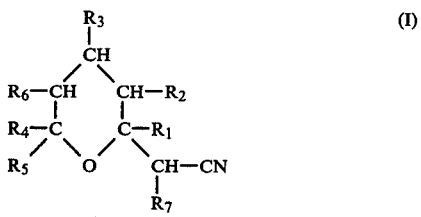

wherein $R_1$ is alkyl and each of $R_2$, $R_3$, $R_4$, $R_5$, $R_6$ and $R_7$ is hydrogen or alkyl which consists of reacting an aliphatic 1,5-hydroxyketone of the formula (II):

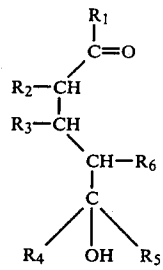

wherein $R_1$, $R_2$, $R_3$, $R_4$, $R_5$ and $R_6$ are as defined above with an aliphatic nitrile of the formula $R_7$-$CH_2CN$ wherein $R_7$ is hydrogen or alkyl in the presence of an alkali metal or alkaline earth metal hydroxide or alcoholate at a temperature between 30° C. and 150° C. and wherein the molar ratio of aliphatic nitrile to hydroxyketone is between 2 and 100.

2. A process as claimed in claim 1 wherein the quantity of said alkali metal or alkaline earth metal hydroxide or alcoholate is between 1 and 20 mol % of the initial hydroxyketone.

3. A process as claimed in claim 1 wherein said molar ratio of aliphatic nitrile to hydroxyketone is between 5 and 30.

4. A process as claimed in claim 1 wherein said reaction temperature is between 50° and 120° C.

5. A process as claimed in claim 1 wherein on termination of the reaction, both the unconverted hydroxyketone and the formed pyran nitrile are removed by distillation, and the distillation residue is recycled to the feed stream for the pyran nitrile preparation reaction.

* * * * *